United States Patent [19]

Rochat et al.

[11] Patent Number: 5,017,706
[45] Date of Patent: May 21, 1991

[54] MONOKETOPYRROLOPYRROLES

[75] Inventors: Alain C. Rochat, Fribourg; Abul Iqbal, Arconciel; Olof Wallquist, Marly, all of Switzerland

[73] Assignee: Ciba-Geigy Corporation, Ardsley, N.Y.

[21] Appl. No.: 332,199

[22] Filed: Apr. 3, 1989

[30] Foreign Application Priority Data

Apr. 12, 1988 [CH] Switzerland .......................... 1334/88

[51] Int. Cl.$^5$ .................. C07D 401/02; C07D 487/04
[52] U.S. Cl. ..................................... 548/414; 548/453; 546/271
[58] Field of Search .................. 548/453, 414; 546/271

[56] References Cited

U.S. PATENT DOCUMENTS

| | | | |
|---|---|---|---|
| 4,415,685 | 11/1983 | Iqbal et al. | 524/92 |
| 4,579,949 | 4/1986 | Rochat et al. | 546/167 |
| 4,585,878 | 4/1986 | Jost et al. | 548/453 |
| 4,632,893 | 12/1986 | Rochat et al. | 430/58 |
| 4,659,775 | 4/1987 | Phenninger et al. | 524/92 |
| 4,666,455 | 5/1987 | Jost et al. | 8/506 |
| 4,720,305 | 1/1988 | Iqbal et al. | 106/288 |
| 4,760,004 | 7/1988 | Rochat et al. | 430/58 |
| 4,791,204 | 12/1988 | Jost et al. | 548/101 |
| 4,810,802 | 3/1989 | Wallquist et al. | 548/453 |

OTHER PUBLICATIONS

F. Closs et al., Angew. Chem. 99. 564 (1987).

*Primary Examiner*—David B. Springer
*Attorney, Agent, or Firm*—Luther A. R. Hall

[57] ABSTRACT

PYRROLOPYRROLES OF THE FORMULA

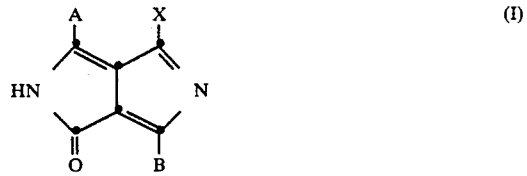

or

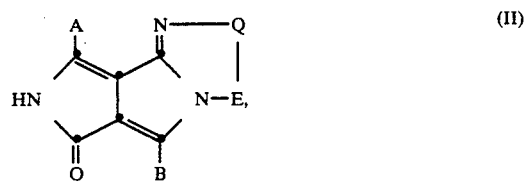

wherein A and B independently of one another are carbocyclic or heterocyclic aromatic radicals, acyclic or cyclic aliphatic radicals or araliphatic radicals, Q is a divalent carbocyclic or heterocyclic aromatic, acyclic or cyclic aliphatic or araliphatic radical, E is a direct bond or a group —CO— or —CS— and X is a group —SR or —NRR', wherein R and R' independently of one another are hydrogen, carbocyclic or heterocyclic aromatic radicals, acyclic or cyclic aliphatic radicals or araliphatic radicals and R' can additionally be a group —O—halogen or —Q—EY—($C_1$-$C_5$-alkyl), wherein Y is O or S, or R and R' form a 5-membered or 6-membered heterocyclic radical with the N atom to which they are bonded.

Pyrrolopyrroles of this type are suitable for coloring high-molecular organic material to give intensely colored, brilliant and transparent colorations with good general fastness properties, and for use in photoelectric recording materials as photoconductive substances.

8 Claims, No Drawings

MONOKETOPYRROLOPYRROLES

The present invention relates to novel 1-keto-4-thioketo- or 1-keto-4-mercapto- and 1-keto-4-amino-pyrrolo[3,4-c]pyrroles and to their use for dyeing high-molecular organic material or as photoconductive substances, and to the intermediates for their preparation.

1,4-Diketopyrrolo[3,4-c]pyrroles and their use as pigments are known e.g. from U.S. Pat. Nos. 4,415,685, 4,579,949, 4,720,305 and 4,659,775 and European patent application A-232 222. 1,4-Dithioketopyrrolo[3,4-c]pyrroles and their suitability as photoconductive substances are described for example in U.S. Pat. Nos. 4,632,893 and 4,760,004.

In Angew. Chem. 99 (1987) no. 6, 567F. Closs and R. Gompper describe the reaction of 1,4-diketo-3,6-diphenylpyrrolo[3,4-c]pyrrole with phosphorus oxychloride and phosphorus pentachloride in the presence of diethylaniline, in which one of the two pyrrole rings is opened.

It has now been found, surprisingly, that a keto group of 1,4-diketopyrrolo[3,4-c]pyrrole can be replaced without ring opening to give novel and interesting monoketopyrrolopyrroles. These novel products can be used as colourants for colouring high-molecular organic material, especially synthetic polymers and preferably polyolefins, polyesters and polyamides, and, in particular when the keto group is replaced with a thioketo group (which was hitherto impossible), can also be incorporated in photoelectric recording materials as photoconductive substances.

The present invention accordingly relates to pyrrolopyrroles of the formula

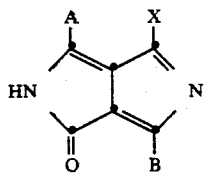

(I)

or

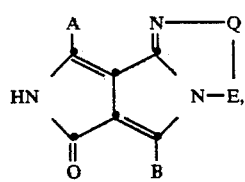

(II)

wherein A and B independently of one another are carbocyclic or heterocyclic aromatic radicals, acyclic or cyclic aliphatic radicals or araliphatic radicals, Q is a divalent carbocyclic or heterocyclic aromatic, acyclic or cyclic aliphatic or araliphatic radical, E is a direct bond or a group —CO— or —CS— and X is a group —SR or —NRR', wherein R and R' independently of one another are hydrogen, carbocyclic or heterocyclic aromatic radicals, acyclic or cyclic aliphatic radicals or araliphatic radicals and R' can additionally be a group —Q—halogen or —Q—EY—($C_1$–$C_5$-alkyl), wherein Y is O or S, or R and R' form a 5-membered or 6-membered heterocyclic radical with the N atom to which they are bonded.

A, B, R and R' as carbocyclic aromatic radicals are e.g. mono-, bi-, tri- or tetra-cyclic radicals, especially monocyclic or bicyclic radicals such as phenyl, biphenyl or naphthyl.

A, B, R and R' as heterocyclic aromatic radicals are e.g. monocyclic to tricyclic. These can be purely heterocyclic or can contain a heterocyclic ring and one or more fused benzene rings, it being possible for them to be bonded either via the heterocyclic moiety or via the carbocyclic moiety. Examples of heterocyclic aromatic radicals are pyridyl, pyrimidyl, pyrazinyl, triazinyl, furyl, pyrrolyl, thiophenyl, quinolyl, coumarinyl, benzofuryl, benzimidazolyl, benzoxazolyl, dibenzofuryl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, quinolinyl, quinazolyl, quinoxalyl, phthalazinyl, phthalazinedionyl, phthalamidyl, chromonyl, naphtholactamyl, quinolonyl, ortho-sulfobenzimidyl, maleimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, anthraquinonyl, acridinyl, acridonyl, quinazolinedionyl, quinoxalinedionyl, benzoxazinedionyl, benzoxazinonyl and naphthalimidyl.

A, B, R and R' as acyclic aliphatic radicals are e.g. branched or unbranched, saturated or unsaturated aliphatic radicals, especially $C_1$–$C_{18}$-alkyl groups such as methyl, ethyl, n-propyl, isopropyl, n-butyl, sec-butyl, tert-butyl, tert-amyl, n-pentyl, n-hexyl, n-octyl, 1,1,3,3-tetramethylbutyl, nonyl, decyl, undecyl, dodecyl, tetradecyl, hexadecyl and octadecyl, or $C_2$–$C_{12}$-alkenyl groups such as vinyl, allyl, prop-1-enyl, 1-methylvinyl, but-2-enyl, pent-2-enyl, hex-3-enyl, oct-2-enyl and dodec-2-enyl.

A, B, R and R' as cyclic aliphatic radicals are e.g. $C_5$–$C_6$-cycloalkyl such as cyclopentyl or especially cyclohexyl.

A, B, R and R' as araliphatic radicals are, for example, $C_7$–$C_{18}$-aralkyl and especially 1-phenylethyl, 1,1-dimethylbenzyl, 2-phenylethyl or, in particular, benzyl.

Both the carbocyclic and the heterocyclic aromatic radicals, as well as the araliphatic radicals, can have conventional substituents which do not confer solubility in water, such as:

(1) Halogen atoms, for example chlorine, bromine or fluorine.

(2) Branched or unbranched alkyl groups having preferably 1 to 18, especially 1 to 12, in particular 1 to 8 and most preferably 1 to 5 C atoms. These alkyl groups can have substituents which do not confer solubility in water, such as fluorine, hydroxyl, cyano, —OCOR$_1$, —OR$_2$, —COOR$_1$, —CONR$_2$R$_3$ or —O-CONHR$_1$, wherein R$_1$ is alkyl, phenyl which is unsubstituted or substituted by halogen, alkyl or —O-alkyl, or naphthyl, and R$_2$ and R$_3$ are hydrogen, alkyl which is unsubstituted or substituted by cyano or hydroxyl, $C_5$–$C_6$-cycloalkyl or phenyl which is unsubstituted or substituted by halogen, alkyl or —O-alkyl, or wherein R$_2$ and R$_3$, together with the N atom, form a 5-membered or 6-membered heterocyclic ring, for example a morpholine, piperidine or phthalimide ring. Other possible substituents on the alkyl groups are monoalkylated or dialkylated amino groups, phenyl which is unsubstituted or substituted by halogen, alkyl or —O-alkyl, naphthyl or else heterocyclic aromatic radicals such as the thien-2-yl, benzoxazol-2-yl, benzthiazol-2-yl, benzimidazol-2-yl, benzimidazolon-6-yl, pyrid-2-yl, -3-yl or -4-yl or quinol-2-yl, -4-yl or -6-yl radicals.

If the substituents mentioned under (2) in turn contain alkyl, this alkyl can be branched or unbranched and can preferably contain 1 to 18, especially 1 to 12, in particular 1 to 8 and most preferably 1 to 5 C atoms.

Examples of unsubstituted or substituted alkyl groups are methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl or benzyl.

(3) The cyano group.

(4) The group of the formula $-NR_2R_3$, wherein $R_2$ and $R_3$ are as defined under (2). Examples are: amino, methylamino, dimethylamino, ethylamino, diethylamino, isopropylamino, $\beta$-hydroxyethylamino, $\beta$-hydroxypropylamino, N,N-bis($\beta$-hydroxyethyl)amino, N,N-bis($\beta$-cyanoethyl)amino, cyclohexylamino, phenylamino, N-methylphenylamino, benzylamino, dibenzylamino, piperidyl, 2,2,6,6-tetramethylpiperid-1-yl or -4-yl or morpholyl.

(5) The group of the formula $-CYOR_1$, wherein Y is O or S and $R_1$ is as defined under (2). Examples of $R_1$ are: methyl, ethyl, isopropyl, tertbutyl, n-butyl, t-amyl, phenyl, benzyl, furfuryl, 2-(dimethylamino)ethyl or 2-cyanoethyl.

(6) The group $-OR_4$, wherein $R_4$ is hydrogen, alkyl, aryl, for example naphthyl or especially phenyl which is unsubstituted or substituted by halogen, alkyl or $-O$-alkyl, $C_5-C_6$-cycloalkyl, aralkyl or a heterocyclic radical. Alkyl occurring in the definitions of $R_4$ can have e.g. a number of C atoms indicated under (2) as being preferred. Examples of $R_4$ are: methyl, ethyl, n-propyl, isopropyl, trifluoroethyl, phenyl, o-, m- or p-chlorophenyl, o-, m- or p-methylphenyl, $\alpha$-naphthyl or $\beta$-naphthyl, cyclohexyl, benzyl, thienyl or pyranylmethyl.

(7) The group $-SR_4$, wherein $R_4$ is as defined under (6). Examples of $R_4$ are: methyl, ethyl, n-propyl, isopropyl, phenyl, o-, m- or p-chlorophenyl, o-, m- or p-methylphenyl, $\alpha$-naphthyl or $\beta$-naphthyl, cyclohexyl, benzyl, thienyl or pyranylmethyl.

(8) The group of the formula $-CYR_4$, wherein Y is O or S and $R_4$ is as defined under (6). Examples of $R_4$ are: methyl, ethyl, tert-butyl, phenyl, o-, m- or p-chlorophenyl, o-, m- or p-methylphenyl, $\alpha$-naphthyl or $\beta$-naphthyl, 2-cyanoethyl or 2-mercaptoethyl.

(9) The group of the formula $-NR_5CYR_1$, wherein Y is O or S, $R_1$ is as defined under (2) and $R_5$ is hydrogen, alkyl, aryl, for example naphthyl or especially phenyl which is unsubstituted or substituted by halogen, alkyl or $-O$-alkyl, $C_5-C_6$-cycloalkyl, aralkyl or the radical $-COR_1$, it being possible for two radicals $-COR_1$ to form a heterocyclic ring together with the N atom. Alkyl occurring in the definitions of $R_5$ can have e.g. a number of C atoms indicated under (2) as being preferred. Examples are: acetylamino, thioacetylamino, propionylamino, butyrylamino, benzoylamino, thiobenzoylamino, p-chlorobenzoylamino, p-methylbenzoylamino, N-methylacetylamino, N-methylbenzoylamino, N-succinimido or N-phthalimido.

(10) The group of the formula $-NR_4COOR_1$, wherein $R_1$ and $R_4$ are as defined under (2) and (6). Examples are the groups $-NHCOOCH_3$, $-NHCOOC_2H_5$ or $-NHCOOC_6H_5$.

(11) The group of the formula $-NR_4CYNR_2R_3$, wherein Y is O or S and $R_4$, $R_2$ and $R_3$ are as defined under (6) and (2). Examples are: ureido, N-methylureido, N-phenylureido or N,N-2',4'-dimethylphenylureido, as well as the thiocarbonyl analogues thereof.

(12) The group of the formula $-NR_5SO_2R_1$, wherein $R_1$ is as defined under (2) and $R_5$ is as defined under (9). Examples are: methanesulfonylamino, phenylsulfonylamino, p-toluylsulfonylamino or $\beta$-naphthylsulfonylamino.

(13) The groups of the formula $-SO_2R_1$ or $-SOR_1$, wherein $R_1$ is as defined under (2). Examples are: methylsulfonyl, ethylsulfonyl, phenylsulfonyl, 2-naphthylsulfonyl or phenylsulfoxidyl.

(14) The group of the formula $-SO_2OR_1$, wherein $R_1$ is as defined under (2). Examples of $R_1$ are: methyl, ethyl, phenyl, o-, m- or p-chlorophenyl, o-, m- or p-methylphenyl or $\alpha$-naphthyl or $\beta$-naphthyl.

(15) The group of the formula $-CYNR_2R_3$, wherein Y is O or S and $R_2$ and $R_3$ are as defined under (2). Examples are: carbamoyl, N-methylcarbamoyl, N-ethylcarbamoyl, N-phenylcarbamoyl, N,N-dimethylcarbamoyl, N-methyl-N-phenylcarbamoyl, N-$\alpha$-naphthylcarbamoyl or N-piperidylcarbamoyl, as well as the thiocarbonyl analogues thereof.

(16) The group of the formula $-SO_2NR_2R_3$, wherein $R_2$ and $R_3$ are as defined under (2). Examples are: sulfamoyl, N-methylsulfamoyl, N-ethylsulfamoyl, N-phenylsulfamoyl, N-methyl-N-phenylsulfamoyl or N-morpholylsulfamoyl.

(17) The group of the formula $-N=N-R_6$, wherein $R_6$ is the radical of a coupling component or a phenyl radical which is unsubstituted or substituted by halogen, alkyl or $-O$-alkyl. Alkyl occurring in the definitions of $R_6$ can have e.g. a number of C atoms indicated under (2) as being preferred. Examples of $R_6$ are: the acetoacetarylide, pyrazolonyl, pyridonyl, o-hydroxyphenyl or p-hydroxyphenyl, o-hydroxynaphthyl, p-aminophenyl or p-N,N-dimethylaminophenyl radicals.

(18) The group of the formula $-OCOR_1$, wherein $R_1$ is as defined under (2). Examples of $R_1$ are: methyl, ethyl, phenyl, o-, m- or p-chlorophenyl or pyrid-2-yl, -3-yl or -4-yl.

(19) The group of the formula $-OCONHR_1$, wherein $R_1$ is as defined under (2). Examples of $R_1$ are: methyl, ethyl, phenyl or o-, m- or p-chlorophenyl.

The acyclic and cyclic aliphatic radicals can also have conventional substituents which do not confer solubility in water, such as those listed under sections 1, 3 to 16, 18 and 19.

In compounds of formula II, when E is $-CO-$ or $-CS-$, Q is preferably a group of the formula

   (III)

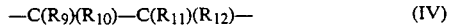   (IV)

or

   (V)

and when E is a direct bond, Q is preferably a group of formula IV or V, in which formulae III to V $R_7$ and $R_8$ independently of one another are hydrogen, $C_1-C_5$-alkyl, $C_5-C_8$-cycloalkyl, phenyl or benzyl which is unsubstituted or substituted by halogen, hydroxyl, $C_1-C_5$-alkyl, $C_1-C_5$-alkoxy or phenoxy, or one of the groups

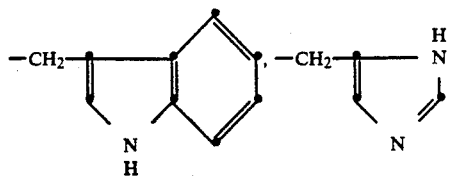

or —(CH$_2$)$_2$S(C$_1$-C$_5$-alkyl), R$_9$, R$_{10}$, R$_{11}$ and R$_{12}$ independently of one another are hydrogen, C$_1$-C$_5$-alkyl, C$_5$-C$_6$-cycloalkyl or phenyl or benzyl which is unsubstituted or substituted by halogen, hydroxyl, C$_1$-C$_5$-alkyl or C$_1$-C$_5$-alkoxy, or R$_{10}$ and R$_{12}$ form a C$_5$-C$_6$-cycloalkylene group together with the C atoms to which they are bonded, and R$_{13}$ and R$_{14}$ independently of one another are hydrogen, C$_1$-C$_5$-alkyl, C$_5$-C$_6$-cycloalkyl or phenyl or benzyl which is unsubstituted or substituted by halogen, hydroxyl, C$_1$-C$_5$-alkyl or C$_1$-C$_5$-alkoxy, or R$_{13}$ *ql and R*$_{14}$, together with the C atoms to which they are bonded, form a naphthalene, anthracene or phenanthrene ring or one of the groups

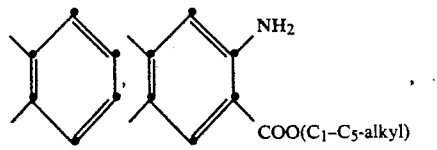

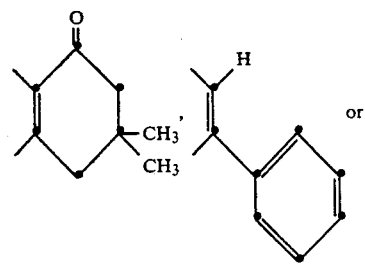

R$_7$, R$_9$ and R$_{11}$ are preferably hydrogen. R$_{13}$ and R$_{14}$ are preferably hydrogen or they preferably form a group

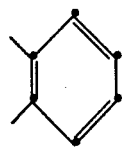

together with the C atoms to which they are bonded.
Examples of radicals Q of formula III are

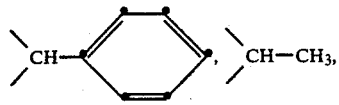

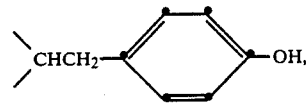

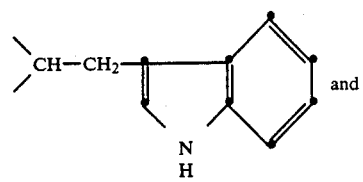

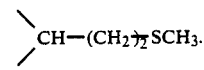

Examples of radicals Q of formula IV are

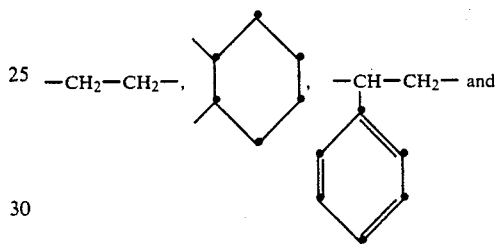

Examples of radicals Q of formula V are

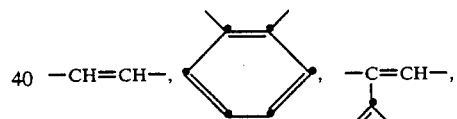

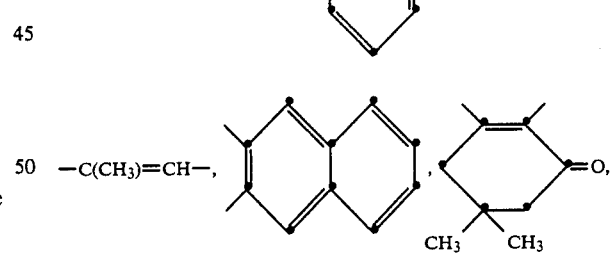

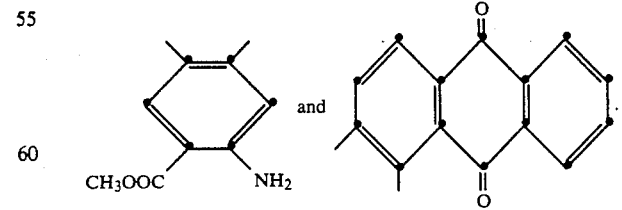

If X in the compound of formula I is a group SH or NHR' (i.e. if R is hydrogen), structural formula I corresponds to only one of its possible tautomeric forms in each case. However, these compounds are also present in the form represented in the following formulae:

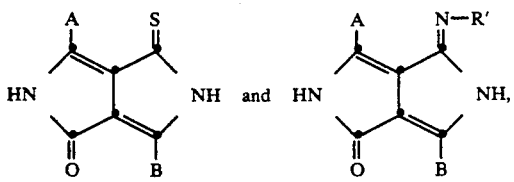

wherein A, B and R' are as defined above, this even being the preferred form in many cases.

Of particular interest are pyrrolopyrroles of formula I or II in which A and B independently of one another are one of the groups

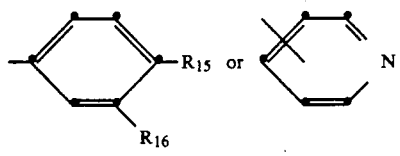

in which $R_{15}$ and $R_{16}$ independently of one another are hydrogen, halogen, nitro, carbamoyl, cyano, trifluoromethyl, $C_2$–$C_{13}$-alkylcarbamoyl, $C_1$–$C_{12}$-alkyl, $C_1$–$C_{12}$-alkoxy, $C_1$–$C_{12}$-alkylmercapto, $C_2$–$C_{13}$-alkoxycarbonyl, $C_2$–$C_{13}$-alkanoylamino, $C_1$–$C_{12}$-monoalkylamino, $C_2$–$C_{24}$-dialkylamino, mono($C_5$–$C_7$-cycloalkyl)amino, di($C_5$–$C_7$-cycloalkyl)amino, N-pyrrolidino, N-piperidino, N-morpholino or phenyl, phenoxy, phenylmercapto, phenoxycarbonyl or phenylcarbamoyl which is unsubstituted or substituted by halogen, $C_1$–$C_{12}$-alkyl or $C_1$–$C_{12}$-alkoxy, X is a group —SR or —NRR', R is hydrogen, $C_1$–$C_{12}$-alkyl, cyclohexyl, β-methoxyallyl, benzyl or phenyl which is unsubstituted or substituted by halogen, cyano, nitro, $C_1$–$C_5$-alkyl, $C_1$–$C_5$-alkoxy, ($C_1$–$C_5$-alkoxy)carbonyl, $C_1$–$C_5$-alkylmercapto, phenylmercapto or phenoxy, or else pyridyl, pyrimidyl, pyrazinyl, triazinyl, furyl, pyrrolyl, thienyl, quinolinyl, coumarinyl, benzofuryl, benzimidazolyl or benzoxazolyl, R' is $C_1$–$C_{12}$-alkyl, β-dimethylaminoethyl, cyclohexyl, cyanoethyl, β-ethoxycarbonylethyl, benzyl, 1-phenyl-2-ethoxycarbonylvinyl or phenyl which is unsubstituted or substituted by halogen, cyano, nitro, $C_1$–$C_5$-alkyl, $C_1$–$C_5$-alkoxy, ($C_1$–$C_5$-alkoxy)carbonyl, $C_1$–$C_5$-alkylmercapto, phenoxy or phenylmercapto, or else pyridyl, pyrimidyl, quinolinyl, pyrazinyl, triazinyl, furyl, pyrrolyl, thienyl, coumarinyl, benzofuryl, anthraquinonyl, benzimidazolyl or benzoxazolyl, or a group —Q—EY—($C_1$–$C_5$-alkyl), or R and R', together with the N atom, form a piperidine, 2,2,6,6-tetramethylpiperidine, pyrrole, morpholine, pyrrolidine or phthalimide ring, E and Y are as defined above and Q is o-phenylene which is unsubstituted or substituted by halogen, cyano, nitro, $C_1$–$C_5$-alkyl, $C_1$–$C_5$-alkoxy or ($C_1$–$C_5$-alkoxy)carbonyl, or a divalent group of the formula —C($R_7$)($R_8$)— or —$CR_{13}$=$CR_{14}$— in which $R_7$ and $R_8$ independently of one another are hydrogen, $C_1$–$C_5$-alkyl or phenyl and $R_{13}$ and $R_{14}$ independently of one another are hydrogen, $C_1$–$C_5$-alkyl or phenyl or form a naphthalene, anthracene or phenanthrene ring together with the C atoms to which they are bonded.

Examples of $C_1$–$C_5$-alkyl groups are methyl, ethyl, n-propyl, isopropyl, n-butyl, sec-butyl, tert-butyl, n-pentyl and tert-amyl and additional examples of $C_1$–$C_{12}$-alkyl groups are n-hexyl, 1,1,3,3-tetramethylbutyl, n-heptyl, n-octyl, nonyl, decyl, undecyl and dodecyl.

Examples of $C_5$–$C_6$-cycloalkyl groups are cyclopentyl and especially cyclohexyl.

$C_1$–$C_5$-alkoxy groups are e.g.: methoxy, ethoxy, propoxy, isopropoxy, n-butoxy, sec-butoxy, tert-butoxy, n-pentoxy and tert-amyloxy and additional examples of $C_1$–$C_{12}$-alkoxy groups are n-hexyloxy, n-heptyloxy, n-octyloxy, decyloxy and dodecyloxy.

$C_1$–$C_5$-alkylmercapto is e.g. methylmercapto, ethylmercapto, propylmercapto, isopropylmercapto, n-butylmercapto, sec-butylmercapto, tert-butylmercapto or tert-amylmercapto.

Examples of $C_2$–$C_{13}$-alkylcarbamoyl groups are N-methylcarbamoyl, N-ethylcarbamoyl, N,N-dimethylcarbamoyl, N-butylcarbamoyl, N,N-dibutylcarbamoyl and N,N-dihexylcarbamoyl.

$C_1$–$C_{12}$-alkylmercapto is e.g. methylmercapto, ethylmercapto, propylmercapto, butylmercapto, n-pentylmercapto, tert-amylmercapto, n-hexylmercapto, decylmercapto or dodecylmercapto.

$C_2$–$C_{13}$-alkoxycarbonyl groups are e.g. methoxy-, ethoxy-, propoxy-, isopropoxy-, n-butoxy-, tert-butoxy-, n-hexyloxy-, n-octyloxy- and dodecyloxy-carbonyl.

$C_2$–$C_{13}$-alkanoylamino is e.g. acetylamino, propionylamino or butyrylamino.

$C_1$–$C_{12}$-monoalkylamino is e.g. methylamino, ethylamino, isopropylamino, n-butylamino, n-octylamino or n-decylamino.

Mono($C_5$–$C_7$-cycloalkyl)amino is e.g. cyclohexylamino.

$C_1$–$C_{12}$-dialkylamino is e.g. dimethylamino, diethylamino, dibutylamino or dihexylamino.

Di($C_5$–$C_7$-cycloalkyl)amino is e.g. dicyclohexylamino.

Halogen is e.g. fluorine, bromine or especially chlorine.

Preferred pyrrolopyrroles of formula I or II are those in which A and B are identical and are one of the groups

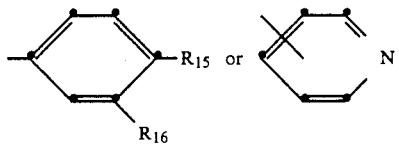

in which one of the substituents $R_{15}$ and $R_{16}$ is a hydrogen, chlorine or bromine atom or a methyl, methoxy, methylmercapto, cyano, phenyl, phenoxy or phenylmercapto group and the other is a hydrogen atom, X is a group —SH or —NHR', R' is $C_1$–$C_{12}$-alkyl, phenyl which is unsubstituted or substituted by halogen, cyano, nitro, methyl, methoxy, methylmercapto, methoxycarbonyl or ethoxycarbonyl, or a group —Q—EY($C_1$–$C_5$-alkyl), E and Y are as defined above and Q is o-phenylene or a divalent group of the formula —CHR$_8$— or —CR$_{13}$=CR$_{14}$— in which
R$_8$ is hydrogen, methyl or phenyl and
R$_{13}$ and R$_{14}$ are hydrogen, methyl or phenyl.

Especially preferred pyrrolopyrroles of formula I or II are those in which A and B are identical and are a group

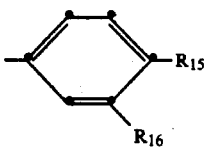

in which
one of the substituents R$_{15}$ and R$_{16}$ is a hydrogen or chlorine atom or a methyl, cyano or phenyl group and the other is a hydrogen atom,
X is a group —SH or NHR',
R' is phenyl which is unsubstituted or substituted by chlorine, bromine, methyl, cyano, nitro, methoxy, methylmercapto, methoxycarbonyl or ethoxycarbonyl,
E is as defined above and
Q is o-phenylene.

The pyrrolopyrroles of formulae I and II can be prepared e.g. by the following processes:

(a) Reaction of a pyrrolopyrrole of the formula

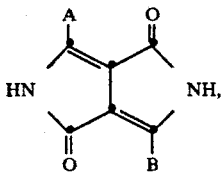

(VI)

wherein A and B are as defined above, with a compound of the formula DG (VII), wherein D is chlorine or bromine and G is a group —SOCl, —SOBr, —POCl$_2$, —POClBr, —POBr$_2$, —POClZ or —POBrZ, wherein Z is phenyl, phenoxy, phenylmercapto, di(C$_1$-C$_4$-alkyl)amino, phenylamino, diphenylamino or phenyl(C$_1$-C$_4$-alkyl)amino, it also being possible for the phenyl groups to be substituted by halogen or C$_1$-C$_5$-alkyl, in the presence of a suitable catalyst, preferably a secondary amide such as dimethylformamide, dimethylacetamide or N-methylpyrrolidone, gives a pyrrolopyrrole of the formula

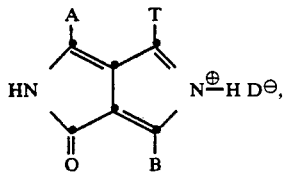

(VIII)

wherein A and B are as defined above and T is chlorine, bromine or a group —O—G, wherein G is as defined above. D is preferably chlorine and G is preferably a group —POClZ in which Z is phenyl, phenoxy, dimethylamino or phenylamino, or especially a group —POCl$_2$.

(b) Reaction of the intermediate of formula VIII, by methods known per se, with a compound of the formula

HSR    (IX)

or

HNRR'    (X), wherein R and R' are as defined above, or with salts of the compounds of formula IX or X, gives the corresponding compound of formula I, after neutralization to avoid the isolation of a hydrohalide.

(c) Heating pyrrolopyrroles of formula I in which X is a group —NH—Q— halogen or —NH—Q—EY—(C$_1$-C$_5$-alkyl) in a suitable organic solvent, optionally in the presence of a suitable catalyst, by commonly known cyclization methods, gives the corresponding compound of formula II by cyclization.

The compounds of formulae VI, VII, IX and X are known. If some of these compounds are novel, they can be prepared analogously to commonly known methods.

If salts of the compounds of formula IX or X are used for step (b), they are advantageously e.g. the alkali metal salts in the case of the compounds of formula IX and e.g. the hydrochlorides in the case of the compounds of formula X.

Examples of suitable solvents for step (b) are water or anhydrous organic solvents which are inert towards the compounds of formula VIII, e.g. the halogenated aliphatic hydrocarbons dichloroethane, tetrachloroethane, chloroform or carbon tetrachloride, or especially tetrahydrothiophene 1,1-dioxide, which is known by the name sulfolan.

In the reaction with compounds of formula IX in which R is hydrogen, it is recommended to use the corresponding alkali metal salts, e.g. sodium or potassium sulfide.

Cyclizations according to step (c) are advantageously carried out using suitable catalysts. For cyclizations of compounds of formula I in which X is a group —NH—Q—halogen, suitable catalysts are e.g. metallic copper, copper halides or mixtures thereof. For cyclizations of compounds of formula I in which X is a group —NH—Q—EY-(C$_1$-C$_5$-alkyl), acid catalysts, e.g. glacial acetic acid or p-toluenesulfonic acid, are particularly suitable.

The preparation, described above, of compounds of formula I can be carried out either stepwise, with or without isolation of the intermediate of formula VIII, or in a one-pot process. Sulfolan has proved the most suitable solvent for the one-pot process.

The pyrrolopyrroles formed as intermediates, of the formula

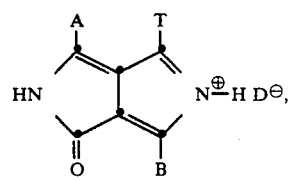

(VIII)

wherein A and B independently of one another are carbocyclic or heterocyclic aromatic radicals, acyclic or cyclic aliphatic radicals or araliphatic radicals and T is chlorine, bromine or a group —O—G, wherein G is a group —SOCl, —SOBr, —POCl$_2$, —POClBr, —POBr$_2$, —POClZ or —POBrZ, wherein Z is phenyl, phenoxy, phenylmercapto, di(C$_1$-C$_4$-alkyl)amino, phenylamino, diphenylamino or phenyl(C$_1$-C$_4$-alkyl)amino, it also being possible for the phenyl groups to be substituted by halogen or C$_1$-C$_5$-alkyl, are novel and represent a further subject of the present invention.

Of particular interest as intermediates are pyrrolopyrroles of formula VIII in which A and B independently of one another are one of the groups

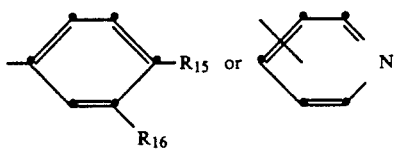

in which R$_{15}$ and R$_{16}$ independently of one another are hydrogen, halogen, nitro, carbamoyl, cyano, trifluoromethyl, C$_2$-C$_{13}$-alkylcarbamoyl, C$_1$-C$_{12}$-alkyl, C$_1$-C$_{12}$-alkoxy, C$_1$-C$_{12}$-alkylmercapto, C$_2$-C$_{13}$-alkoxycarbonyl, C$_2$-C$_{13}$-alkanoylamino, C$_1$-C$_{12}$-monoalkylamino, C$_2$-C$_{24}$-dialkylamino, mono(C$_5$-C$_7$-cycloalkyl)amino, di(C$_5$-C$_7$-cycloalkyl)amino, N-pyrrolidino, N-piperidino, N-morpholino or phenyl, phenoxy, phenylmercapto, phenoxycarbonyl or phenylcarbamoyl which is unsubstituted or substituted by halogen, C$_1$-C$_{12}$-alkyl or C$_1$-C$_{12}$-alkoxy, and T is as defined above.

Preferred intermediates are pyrrolopyrroles of formula VIII in which A and B are identical and are one of the groups

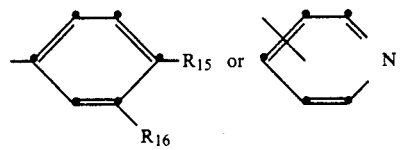

in which one of the substituents R$_{15}$ and R$_{16}$ is a hydrogen, chlorine or bromine atom or a methyl, methoxy, methylmercapto, cyano, phenyl, phenoxy or phenylmercapto group and the other is a hydrogen atom and T is chlorine or a group —O—G in which G is one of the groups —POCl$_2$ or POClZ in which Z is phenyl, phenoxy or phenylamino.

Especially preferred intermediates are pyrrolopyrroles of formula VIII in which A and B are identical and are a group

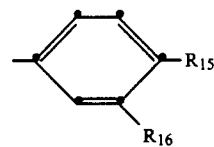

in which one of the substituents R$_{15}$ and R$_{16}$ is a hydrogen or chlorine atom or a methyl, cyano or phenyl group and the other is a hydrogen atom and T is chlorine or a group —O—POCl$_2$.

The pyrrolopyrroles of formulae I and II, and, among those of formula I, especially the ones in which X is a group —NRR', are suitable for colouring high-molecular organic material, especially synthetic polymers such as polycarbonates, polyacrylates, polymethacrylates, ABS, polyether-ketones, polyurethanes, polyolefins, polyesters and polyamides, individually or in mixtures, including engineering plastics in particular, producing intensely coloured, brilliant transparent colourations with good general fastness properties. The colouring of polyolefins, polyesters and polyamides is especially preferred. However, the said compounds can also be used for colouring lacquers and printing inks.

Colouring is carried out by the conventional processes, for example by mixing the colourant with the granulated or powdered plastic and extruding the mixture to give fibres, sheets or granules. The latter can then be injection-moulded to form articles.

The colourations obtained, for example in plastics, fibres, lacquers or inks, are distinguished by a yellow to blue shade, a very high colour strength, high saturation, good dispersibility and a good fastness to overpainting, migration, heat, light and weather, and by a good brightness and good IR reflectance properties.

The compounds of formulae I and II can also be used as photoelectrophoretic toners.

When the compounds of formulae I and II are present in solution in the polymers used, they are also distinguished by a clear shade, a high colour strength and good fastness properties, especially fastness to light and sublimation, and also by high fluorescence. They are suitable for use in solar energy collectors and for the production of laser beams.

As already mentioned, the pyrrolopyrroles of formulae I and II, especially those of formula I in which X is a group —SH, also have a photoconductive action. Accordingly they can be incorporated as photoconductive substances, for example in electrophotographic recording materials. The structure of such electrophotographic recording materials, the possible ways of incorporating the photoconductive substances and their mode of action are described in European patent application A-187 620 with reference to dithioketopyrrolopyrroles. The same principles apply to the thioketopyrrolopyrroles of the invention.

The following Examples will serve to illustrate the invention.

EXAMPLE 1

28.8 g of 1,4-diketo-3,6-diphenylpyrrolo[3,4-c]pyrrole and 275 ml of phosphorus oxychloride are placed in a 750 ml sulfonation flask equipped with a stirrer, a thermometer, a reflux condenser and a nitrogen purge. After a catalytic amount of dimethylformamide (~0.2 g) has been added, the suspension is heated to the reflux temperature (105°-106° C.) and stirred for about 20 hours at this temperature, during which time the starting material goes into solution and some of the product formed precipitates. The reaction mixture is cooled to ~4° C. with an ice bath and stirred for about 5 hours at this temperature. The crystalline product is finally isolated by filtration, washed with ether and dried at 80° C. in a vacuum-drying oven with the exclusion of moisture. Yield: 38.6 g (87.5% of theory) of a red product of the formula

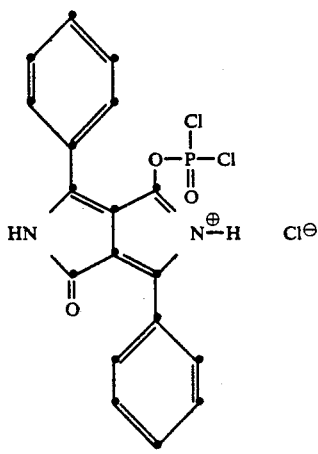

| Elemental analysis: | | |
|---|---|---|
| | calculated | found |
| C | 48.95% | 50.2% |
| H | 2.74% | 2.90% |
| N | 6.34% | 6.33% |
| Cl | 24.1% | 22.3% |
| P | 7.01% | 6.7% |

Melting point: 235°–237° C. (decomp.).

EXAMPLE 2

4.51 g of the product of Example 1 and 40 ml of cold water are placed, under nitrogen, in a 200 ml sulfonation flask equipped with a stirrer. The suspension is cooled to 2°–4° C. with an ice bath and an aqueous sodium sulfide solution made up of 8.03 g of Na₂S.8H₂O and 20 ml of water is then added so that the pH is kept in the range between 8.5 and 11 and the temperature rises spontaneously to 20° C. The sodium sulfide solution is metered in, as described above, until there is no further pH change. After stirring for three hours at 20° C., the reaction mixture is heated to 32°–34° C. and kept at this temperature until the reaction is complete (7 hours in total). The suspension is then cooled to room temperature and filtered and the material on the filter is washed with warm water until the washings are neutral. The moist product is then suspended in 100 ml of glacial acetic acid and subjected to an aftertreatment for 1½ hours at 80° C., the suspension is then cooled to 45° C. and filtered and the material on the filter is washed successively with methanol and with warm water until the washings are neutral. After drying at 80° C. in a vacuum-drying oven, 2.34 g (77% of theory) of a compound of the formula

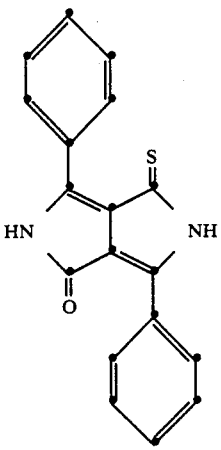

are obtained. Recrystallization from dimethylformamide gives a violet-blue product melting above 300° C. and giving the following analytical data:

| | calculated | found |
|---|---|---|
| C | 71.03% | 71.2% |
| H | 3.97% | 4.05% |
| N | 9.20% | 9.12% |
| S | 10.53% | 10.2% |

EXAMPLE 3

0.65 g of the product of Example 1 and 0.57 g of aniline are refluxed for 3 hours in 10 ml of 1,1,2,2-tetrachloroethane in a round-bottomed flask. After cooling, the reaction product is diluted with acetone, isolated by suction filtration, washed with acetone and then with water until the washings are neutral, and finally purified on an SiO₂ column (eluent: methylene chloride/methanol, 95:5 vol/vol). Yield: 0.22 g of a compound of the formula

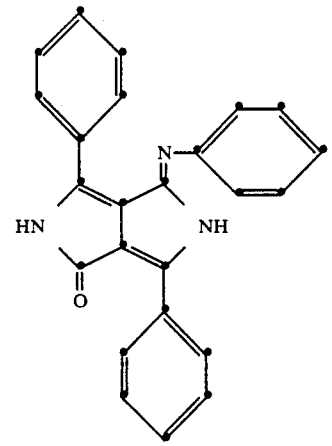

| Elemental analysis: | | |
|---|---|---|
| | calculated | found |
| C | 79.3% | 78.5% |
| H | 4.7% | 4.8% |
| N | 11.6% | 11.4% |

EXAMPLE 4

A mixture consisting of 2.88 g of 1,4-diketo-3,6-diphenylpyrrolo[3,4-c]pyrrole, 4.7 g of phosphorus oxychloride and 25 ml of tetrahydrothiophene 1,1-dioxide (sulfolan) is placed in a 100 ml sulfonation flask under argon. 2 drops of dimethylacetamide (~90 mg) are also added as a catalyst. The mixture is heated to 120° C. and kept for 2 hours at this temperature, during which time the starting pigment goes into solution. After cooling to 115° C., the unreacted phosphorus oxychloride (~1.5 ml) is distilled off under reduced pressure (~200 mbar). While flushing with argon, the contents of the flask are then cooled to approx. 80° C. and 1.46 g of 4-aminobenzonitrile are added. The mixture is heated again to 120° C. and kept for 2 hours at this temperature. The suspension is then cooled to 30° C., poured into ice-cold 5% aqueous ammonia solution and stirred for 15 minutes. The product which has precipitated is then isolated by filtration and washed with water until the filtrate is colourless and neutral. After drying in a vacuum-drying oven at 80° C., 3.9 g (100% of theory) of crude product are obtained. After purification in boiling methanol under reflux, 2.75 g of a violet product of the formula

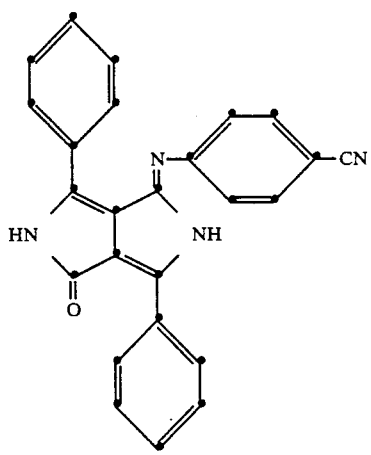

are isolated which melts above 300° C. and gives the following analytical data:

|   | calculated | found |
| --- | --- | --- |
| C | 77.30% | 76.70% |
| H | 4.15% | 4.25% |
| N | 14.42% | 14.65% |

EXAMPLE 5

If Example 4 is repeated exactly except that the 4-aminobenzonitrile is replaced with 1.7 g of 4-nitroaniline, 3.7 g (91.4% of theory) of crude product are isolated by precipitation when the reaction mixture is poured into 5% aqueous ammonia solution. After purification by boiling under reflux in a mixture of methylene chloride and methanol (4:1 vol/vol), 2.5 g of a dark blue product of the formula

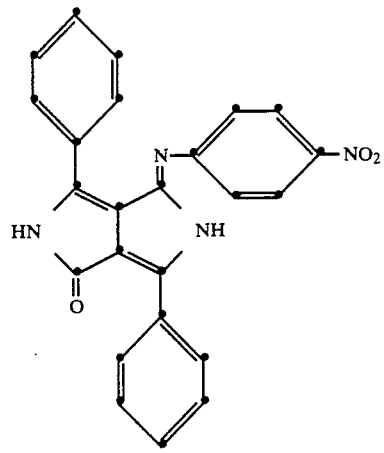

are obtained which melts above 300° C. and gives the following analytical data:

|   | calculated | found |
| --- | --- | --- |
| C | 70.58% | 69.9% |
| H | 3.95% | 3.8% |
| N | 13.72% | 13.5% |

EXAMPLE 6

If Example 4 is repeated exactly except that the 4-aminobenzonitrile is replaced with 1.55 g of 4-chloroaniline, 3.4 g (85.4% of theory) of crude product are isolated by precipitation when the reaction mixture is poured into 5% aqueous ammonia solution. After purification in boiling methanol under reflux, 2.5 g of a reddish blue product of the formula

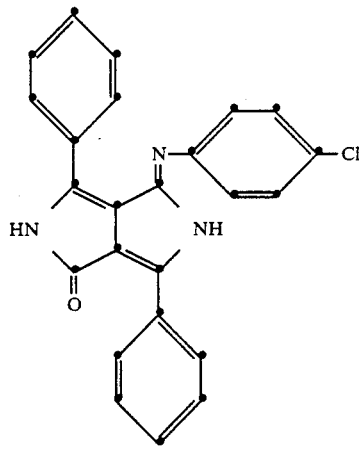

are obtained which melts above 300° C. and gives the following analytical data:

|   | calculated | found |
| --- | --- | --- |
| C | 72.45% | 72.0% |
| H | 4.05% | 4.08% |
| N | 10.56% | 10.25% |
| Cl | 8.91% | 8.75% |

EXAMPLE 7

A mixture of 5.76 g of 1,4-diketo-3,6-diphenylpyrrolo[3,4-c]pyrrole, 4.64 g of phosphorus oxychloride and 50 ml of tetrahydrothiophene, 1,1-dioxide (sulfolan) is placed in a 200 ml sulfonation flask under nitrogen and 4 drops of dimethylacetamide (~180 mg) are then also added as a catalyst. The mixture is heated to 118° C., kept for 13 hours at this temperature and then cooled to room temperature. The unreacted starting material is filtered off and washed with a small amount of warm sulfolan. The filtrate is then treated for 1½ hours on a rotary evaporator at 80° C. under vacuum in order to completely remove any phosphorus oxychloride still present.

The residual solution is placed in a 200 ml sulfonation flask under nitrogen and 8.32 g of technical-grade ethyl anthranilate (~95% pure) are then added. The mixture is heated to 87° C. and kept for 8 hours at this temperature. After cooling to room temperature, the reaction solution is poured into 400 ml of cold water, with vigorous stirring, and the crude product precipitates. The strongly acidic suspension is adjusted to pH 7 with triethanolamine, heated to 50° C., stirred for 1 hour and filtered. The material on the suction filter is washed with water and ethanol and dried at 80° C. in a vacuum-drying oven. Yield: 3.74 g of a violet product of the formula

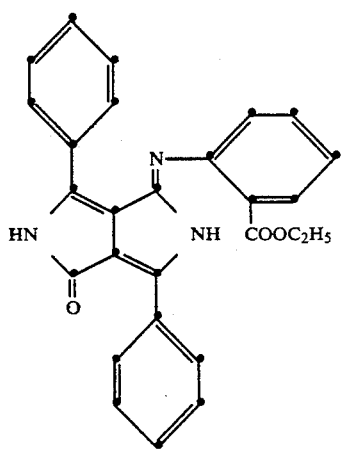

melting at ~235° C. (the sample solidifies again above this temperature) and giving the following analytical data:

|   | calculated | found |
|---|---|---|
| C | 74.47% | 73.30% |
| H | 4.86% | 4.82% |
| N | 9.65% | 9.55% |

EXAMPLE 8

2.22 g of the product of Example 7, 2 ml of glacial acetic acid and 25 ml of pure o-dichlorobenzene are placed in a 100 ml sulfonation flask and stirred vigorously. The resulting suspension is heated to 125° C. and stirring is continued for 4½ hours at this temperature. During this time, the starting material first goes into solution and the cyclized product then precipitates. The reaction mixture is cooled to 50° C. and the crystalline product is isolated by filtration, washed with acetone and methanol until the washings are colourless, and dried in a vacuum-drying oven at 80° C. 1.41 g of a homogeneous violet product of the formula

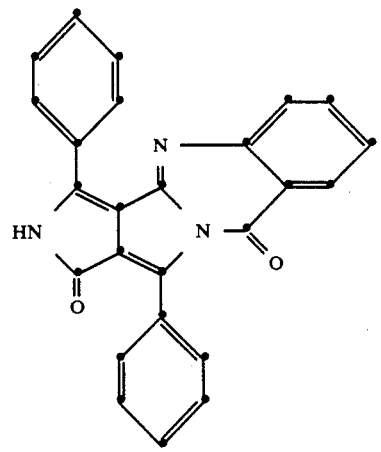

are isolated which melts above 300° C. and gives the following analytical data:

|   | calculated | found |
|---|---|---|
| C | 77.11% | 76.60% |
| H | 3.88% | 3.99% |
| N | 10.79% | 10.73% |

EXAMPLE 9

10 g of 1,4-diketo-3,6-(3,4-dimethylphenyl)pyrrolo[3,4-c]pyrrole in 133 g of phosphorus oxychloride are treated analogously to Example 1 in the presence of 4 drops of dimethylformamide. 6.6 g of a dark red powder are isolated. 2.0 g of this product in 15 ml of ethylene chloride are treated analogously to Example 3 with 0.41 g of aniline in the presence of 0.45 g of triethylamine. 1.50 g (89%) of a dark red product of the formula

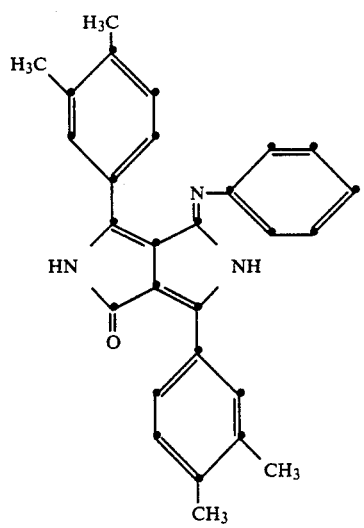

are isolated, the structure of which is confirmed by the mass spectrum (MS: M+ =491).

EXAMPLE 10

1.0 g of the product of Example 1 is refluxed for 20 hours in 10 ml of ethylene chloride with 0.40 g of mercaptobenzthiazole and 0.25 g of triethylamine. After cooling, filtration and washing with acetone, 0.76 g of a mixture of 1,4-diketo-3,6-diphenylpyrrolo[3,4-c]pyrrole and a product of the formula

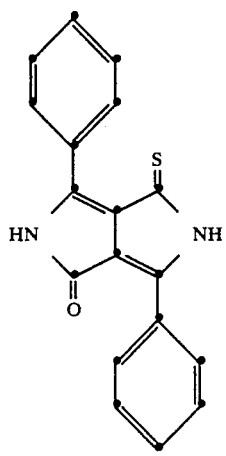

in a ratio of approx. 2:1 (confirmed by MS, ¹H NMR) is isolated.

EXAMPLE 11

10.16 g of the product of Example 1 and 4.60 g of ethyl p-chloroanthranilate are stirred in 300 ml of o-dichlorobenzene for 18 hours at 75° C., with the exclusion of moisture. The reaction mixture is cooled to room temperature and 3.2 ml of triethylamine are added. The reaction mixture is poured into 500 ml of a 1:1 mixture of toluene and ethyl acetate and stirred for 2 hours at 80° C. After cooling to room temperature, the residue is isolated by filtration and washed with 500 ml of a 1:1 mixture of toluene and ethyl acetate. After the residue has been dried in a vacuum-drying oven, 12.60 g of a solid product are obtained. An insoluble by-product is separated off by filtration on a small amount of silica gel with 1:1 methylene chloride/methanol and, after evaporation, 7.3 g of a mixture of the products of the formulae

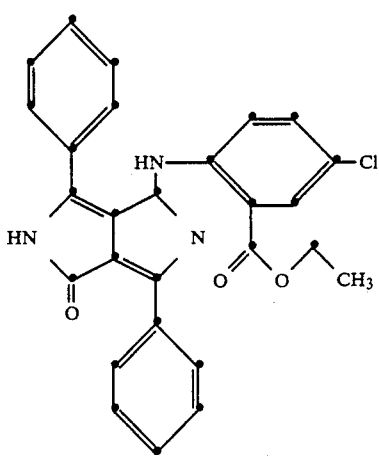

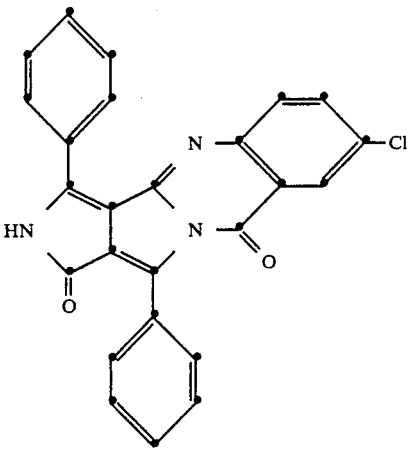

are obtained (mass spectrum: $M^+ = 469$ and $M^+ = 423$).

EXAMPLE 12

5 g of the mixture of Example 11 are suspended in 400 ml of o-dichlorobenzene, 20 ml of acetic acid are added and the mixture is heated for 22 hours at 140° C. After cooling to room temperature, it is filtered and the material on the filter is washed with 400 ml of o-dichlorobenzene and 500 ml of methylene chloride. Drying in a vacuum-drying oven gives 2.24 g of the product of the formula

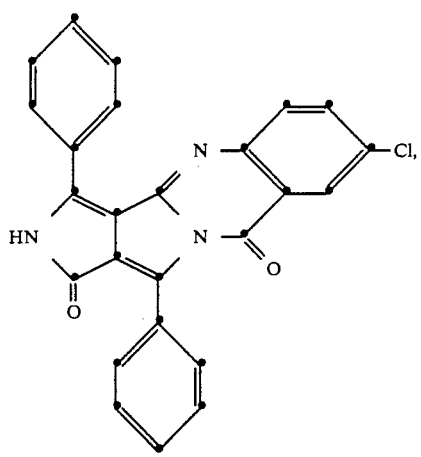

the structure of which is confirmed by MS ($M^+ = 423$).

| Elemental analysis: | calculated | found |
|---|---|---|
| C | 70.84 | 69.05 |
| H | 3.33 | 3.63 |
| N | 9.91 | 9.36 |
| Cl | 8.36 | 8.94 |

EXAMPLE 13

100 g of polyester granules (TERLENKA ® from the company Enka), dried at 110° C. under high vacuum, are mixed with 0.2 g of the product of Example 8 for 30 minutes on a mechanical shaker. The uniformly coloured granules obtained are then extruded in a laboratory extruder of the Weber ET 20 ® type at 260° C. to give a thin, transparent, fluorescent red ribbon. The colouration is distinguished by an intensely coloured, clear shade and good general fastness properties.

A colouration with similar properties is obtained if the product of Example 8 is replaced with the product of Example 7.

EXAMPLE 14

(Use in alkyd-melamine stoving lacquer) 135 g of glass beads (4.5 mm), 400 mg of the product of Example 8, 7.6 g of TiO$_2$ (®Bayertitan R-KB-3), 9.0 ml of methyl isobutyl ketone and 30.0 g of alkyd-melamine stoving lacquer of the composition 67.5% of alkyd resin (®Alkydal F-27), 60% in xylene,
26.5% of melamine resin (®Maprenal TTX), 55% in xylene,
5.0% of xylene and
1.0% of silicone oil, 1% in xylene (solids content=55%) are placed in a 100 ml screw-cap bottle and ground for 16 hours in a vibration grinding mill. The coloured lacquer is drawn out onto an aluminium strip using a film drawing device. After exposure to air, the strip of lacquer is stoved for 30 min. at 130° C. to give a violet coating of lacquer with a good fastness to light and weather.

What is claimed is:

1. A pyrrolopyrrole of formula I

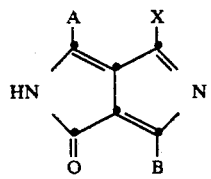

(I)

wherein
A and B are identical and are one of the groups

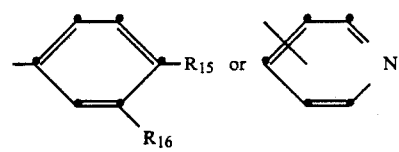

in which one of the substituents $R_{15}$ and $R_{16}$ is a hydrogen, chlorine or bromine atom or a methyl, methoxy, methylmercapto, cyano, phenyl, phenoxy or phenylmercapto group, and the other is a hydrogen atom,
X is a group —SH or —NHR',
R' is $C_1$-$C_{12}$-alkyl, phenyl which is unsubstituted or substituted by halogen, by cyano, by nitro, by methyl, by methoxy, by methylmercapto, by methoxycarbonyl or by ethoxycarbonyl, or R' is a group —Q—EY($C_1$-$C_5$-alkyl),
E is a direct bond or a group —CO— or —CS—,
Y is —O— or —S—, and
Q is o-phenylene or a divalent group of the formula —CHR$_8$— or —CR$_{13}$=CR$_{14}$—, in which R$_8$ is hydrogen, methyl or phenyl, and R$_{13}$ and R$_{14}$ are hydrogen, methyl or phenyl.

2. A pyrrolopyrrole of formula I according to claim 1 in which A and B are identical and are a group

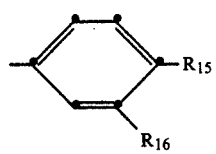

in which
one of the substituents $R_{15}$ and $R_{16}$ is a hydrogen or chlorine atom or a methyl, cyano or phenyl group and the other is a hydrogen atom,
X is a group —SH or —NHR',
R' is phenyl which is unsubstituted or substituted by chlorine, bromine, methyl, cyano, nitro, methoxy, methylmercapto, methoxycarbonyl or ethoxycarbonyl
E is as defined in claim 1 and
Q is o-phenylene.

3. The pyrrolopyrrole according to claim 1 which is

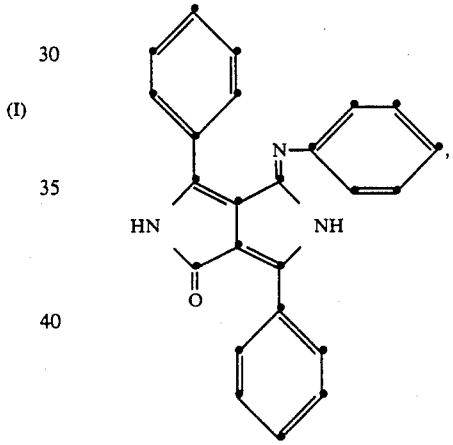

4. The pyrrolopyrrole according to claim 1 which is

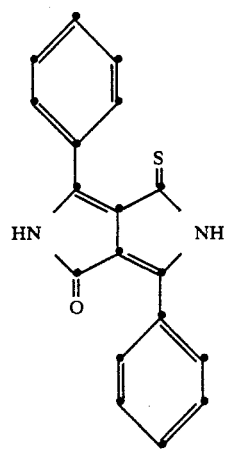

-continued
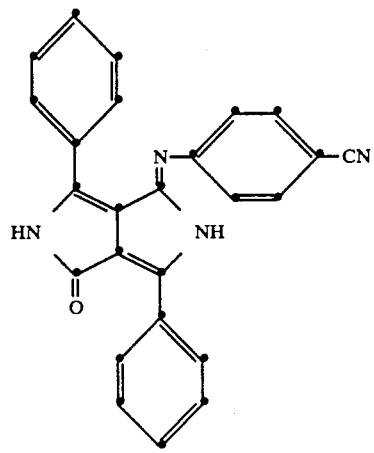
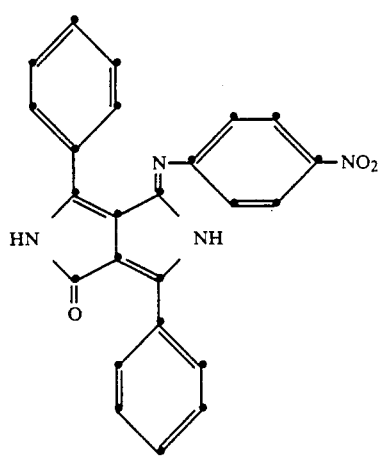
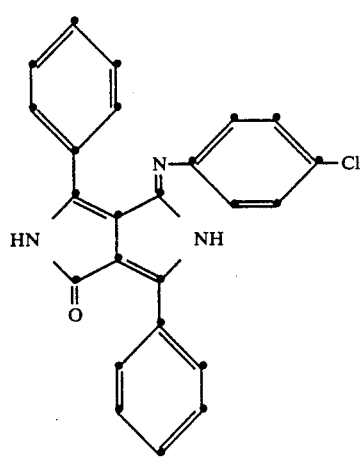
-continued
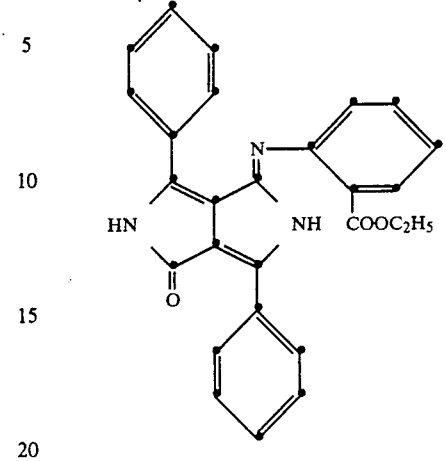
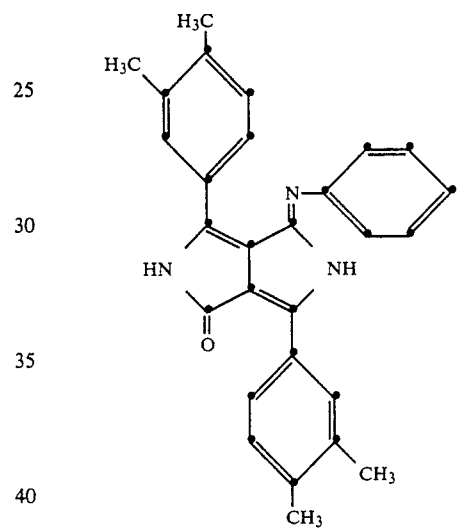
or
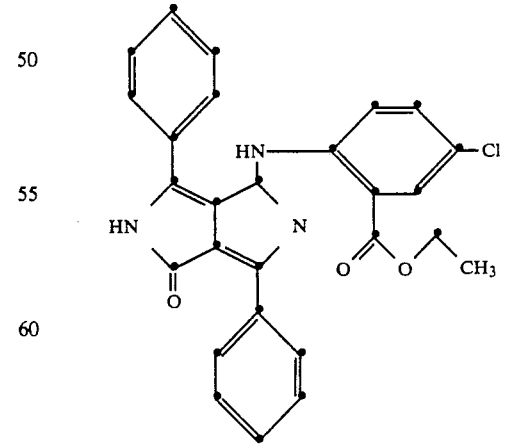
5. A pyrrolopyrrole of formula VIII

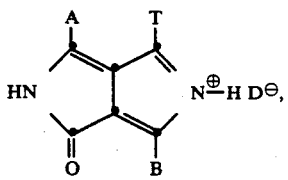

wherein

A and B are identical and are one of the groups

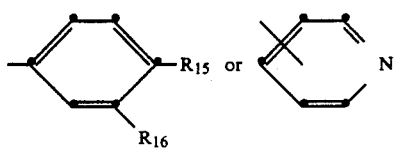

in which one of the substituents $R_{15}$ and $R_{16}$ is a hydrogen, chlorine or bromine atom or a methyl, methoxy, methylmercapto, cyano, phenyl, phenoxy or phenylmercapto group and the other is a hydrogen atom, D is chlorine or bromine, and T is chlorine, bromine or a group —O—G, wherein G is a group —SOCl, —SOBr, —POCl$_2$, —POBr$_2$, —POClZ or —POBrZ, where Z is phenyl, phenoxy, phenylmercapto, di(C$_1$-C$_4$-alkyl)amino, phenylamino, diphenylamino or phenyl(C$_1$-C$_4$-alkyl)amino; or where said phenyl groups are substituted by halogen or by C$_1$-C$_5$-alkyl.

6. A pyrrolopyrrole of formula VIII according to claim 5 in which A and B are identical and are one of the groups

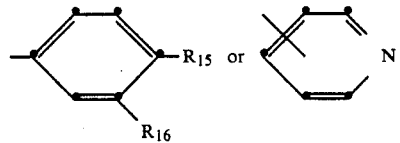

in which one of the substituents $R_{15}$ and $R_{16}$ is a hydrogen, chlorine or bromine atom or a methyl, methoxy, methylmercapto, cyano, phenyl, phenoxy or phenylmercapto group and the other is a hydrogen atom and T is chlorine or a group —O—G in which G is one of the groups —POCl$_2$ or POClZ in which Z is phenyl, phenoxy or phenylamino.

7. A pyrrolopyrrole of formula VIII according to claim 5 in which A and B are identical and are a group

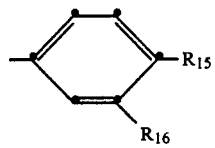

in which one of the substituents $R_{15}$ and $R_{16}$ is a hydrogen or chlorine atom or a methyl, cyano or phenyl group and the other is a hydrogen atom and T is chlorine or a group —O—POCl$_2$.

8. The pyrrolopyrrole according to claim 5 which is

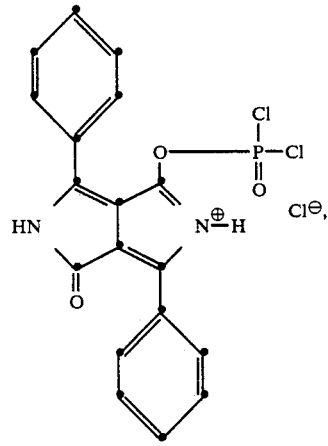

* * * * *